(12) United States Patent
Sugama et al.

(10) Patent No.: US 8,227,463 B2
(45) Date of Patent: Jul. 24, 2012

(54) AMORPHOUS BODY COMPOSED OF HETEROCYCLIC COMPOUND, SOLID DISPERSION AND PHARMACEUTICAL PREPARATION EACH COMPRISING THE SAME, AND PROCESS FOR PRODUCTION OF THE SAME

(75) Inventors: Tadaaki Sugama, Tokyo (JP); Nobuhiro Ishihara, Tokyo (JP); Yoshiharu Tanaka, Tokyo (JP); Masayuki Takahashi, Tokyo (JP); Shinichi Yaguchi, Tokyo (JP); Tetsuo Watanabe, Tokyo (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 167 days.

(21) Appl. No.: 12/744,160

(22) PCT Filed: Nov. 21, 2008

(86) PCT No.: PCT/JP2008/071259
§ 371 (c)(1),
(2), (4) Date: May 21, 2010

(87) PCT Pub. No.: WO2009/066775
PCT Pub. Date: May 28, 2009

(65) Prior Publication Data
US 2010/0249063 A1    Sep. 30, 2010

(30) Foreign Application Priority Data

Nov. 22, 2007 (JP) ................................. 2007-303332

(51) Int. Cl.
*A61K 31/535* (2006.01)
*C07D 413/14* (2006.01)
(52) U.S. Cl. .................. 514/235.8; 514/236.2; 544/113; 544/122
(58) Field of Classification Search .................. 544/113, 544/122; 514/235.8, 236.2
See application file for complete search history.

(56) References Cited

U.S. PATENT DOCUMENTS

| | | |
|---|---|---|
| 6,251,900 B1 | 6/2001 | Kawashima et al. |
| 7,307,077 B2 | 12/2007 | Kawashima et al. |
| 2006/0009440 A1 | 1/2006 | Kawashima et al. |
| 2008/0113987 A1 | 5/2008 | Haruta et al. |
| 2008/0287431 A1 | 11/2008 | Kawashima et al. |
| 2010/0267700 A1 | 10/2010 | Haruta et al. |

FOREIGN PATENT DOCUMENTS

| | | |
|---|---|---|
| WO | 99 05138 | 2/1999 |
| WO | 00 43385 | 7/2000 |
| WO | 02 088112 | 11/2002 |
| WO | 2004 037812 | 5/2004 |
| WO | 2005 095389 | 10/2005 |
| WO | 2006 095906 | 9/2006 |

OTHER PUBLICATIONS

Extended Search Report issued Dec. 23, 2011 in European Patent Application No. 11168461.9-2117.
Lian Yu, et al., "Amorphous Pharmaceutical Solids: Preparation, Characterization and Stabilization", Advanced Drug Delivery Reviews, vol. 48, No. 1, May 16, 2001, XP009065056, pp. 27-42.
Samuel Petit, et al., "The Amorphous State", Polymorphism: in the Pharmaceutical Industry, XP002481458, Jan. 1, 2006, pp. 259-285.
Aditya Mohan Kaushal, et al., "Amorphous Drug Delivery Systems: Molecular Aspects, Design, and Performance", Critical Reviews in Therapeutic Drug Carrier Systems, XP009084405, vol. 21, No. 3, Jan. 1, 2004, pp. 133-193.
Nuernberg, E. et al., "Modificastion of the Physical and Biopharmaceutical Properties of Medicinal Products by Spray Drying", Chem Ind, vol. 33, (XXXIII) No. 12, pp. 794-796, (Dec. 1981) (with partial English translation).
Takeuchi, H. et al., "Particle Design and Manufacture", Chemical Enginneering, vol. 37, No. 6, pp. 496-501, and p. 544, (Jun. 1992) (with partial English translation).
Okamoto, H. et al., "PSWC 2004 Symposium Report on Pharmaceutical Field", Pharm Tech Japan 8 Gatsugo, vol. 20, No. 9, pp. 1783-1785, and p. 1958, (2004) (with partial English translation).

*Primary Examiner* — Rebecca Anderson
(74) *Attorney, Agent, or Firm* — Oblon, Spivak, McClelland, Maier & Neustadt, L.L.P.

(57) ABSTRACT

[Problems] The object is to improve the absorbability of a heterocyclic compound including s-triazine and a pyrimidine derivative in vitro. [Means for Solving Problems] Disclosed is, for example, an amorphous body of a heterocyclic compound as represented by the general formula (I) [wherein each of R's and others is as defined in the description] including s-triazine and a pyrimidine derivative, or a hydrate, a solvate or a pharmaceutically acceptable salt of the heterocyclic compound. Also disclosed is a process for producing the amorphous body. Further disclosed are: a solid dispersion comprising the amorphous body; and a medicinal preparation comprising the solid dispersion.

10 Claims, 6 Drawing Sheets

[Figure 1]
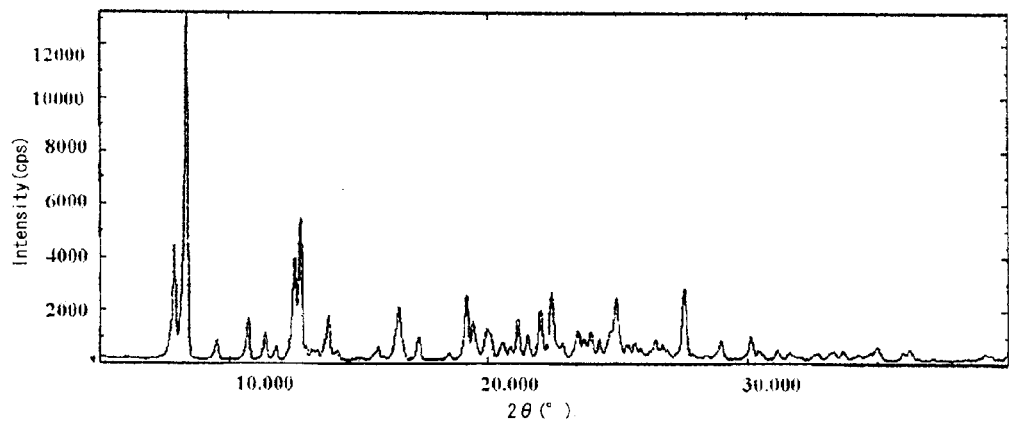
[Figure 2]
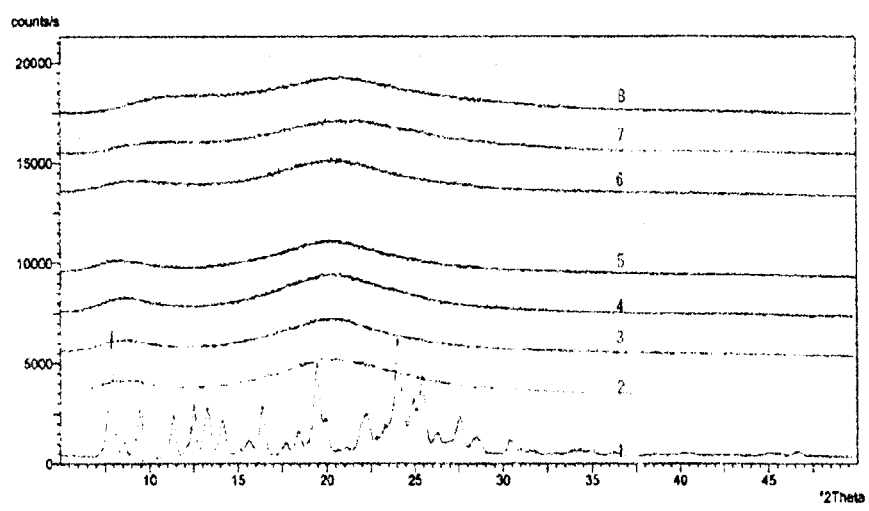

[Figure 3]
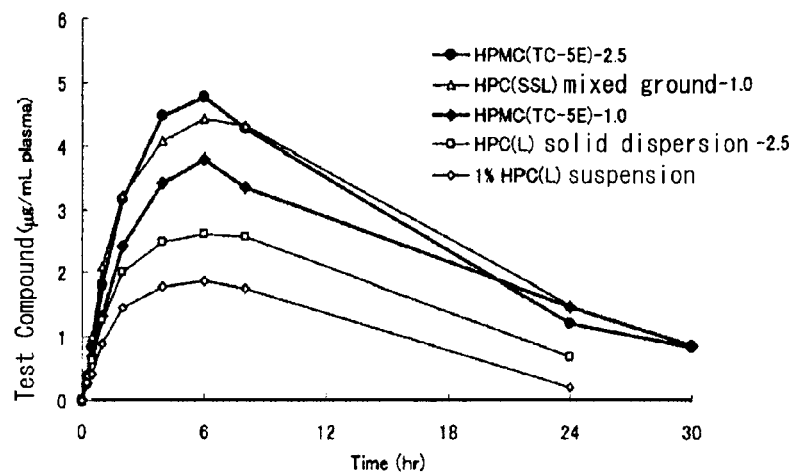
[Figure 4]
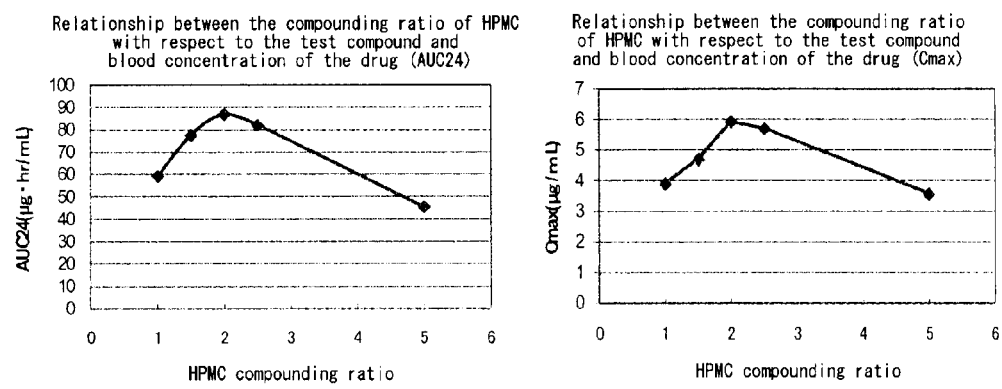

[Figure 5]
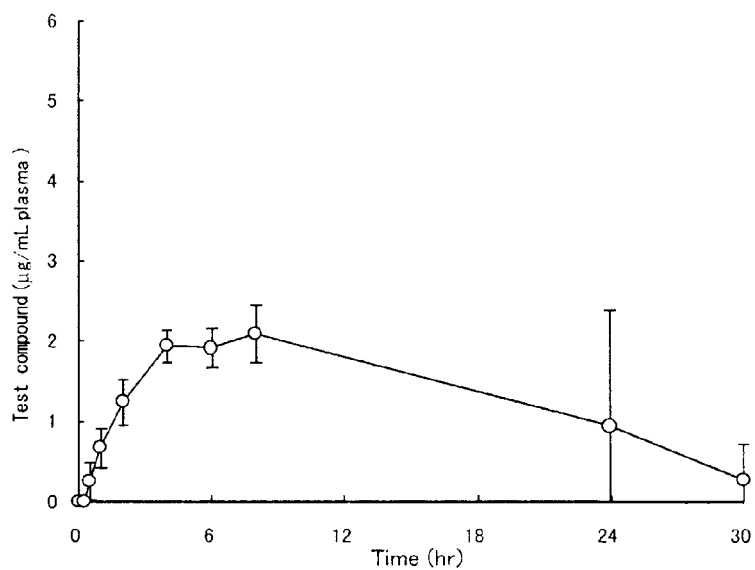
[Figure 6]
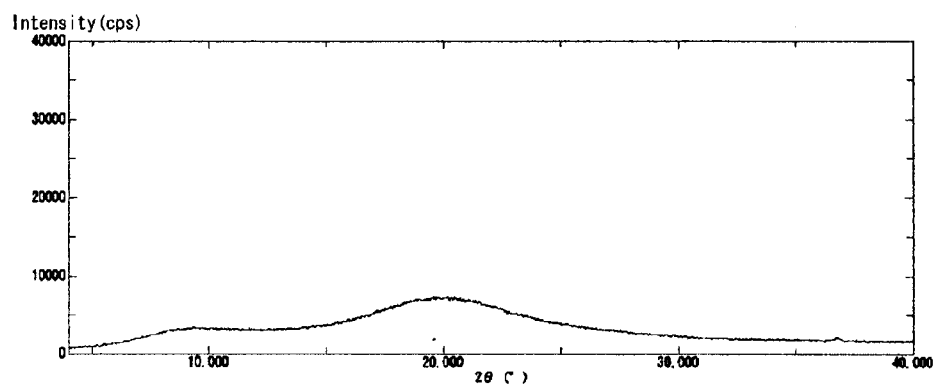
XRD when the test compound was made

[Figure 7]
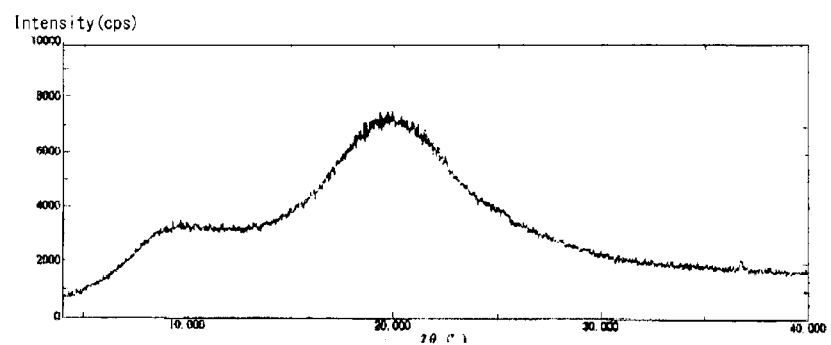
XRD of the amorphous body composed of the test compound, when sealed and stored for 1 month at 40° C(75%RH)
[Figure 8]
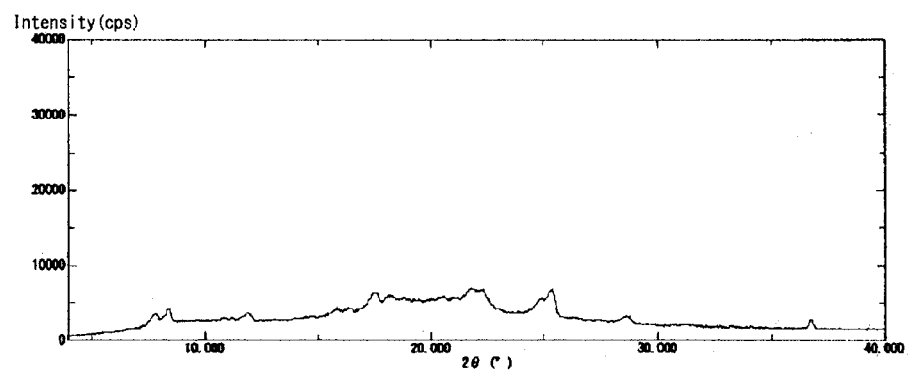
XRD of the amorphous body composed of the test compound, when unsealed and stored for 1 month at 40° C(75%RH)

[Figure 9]
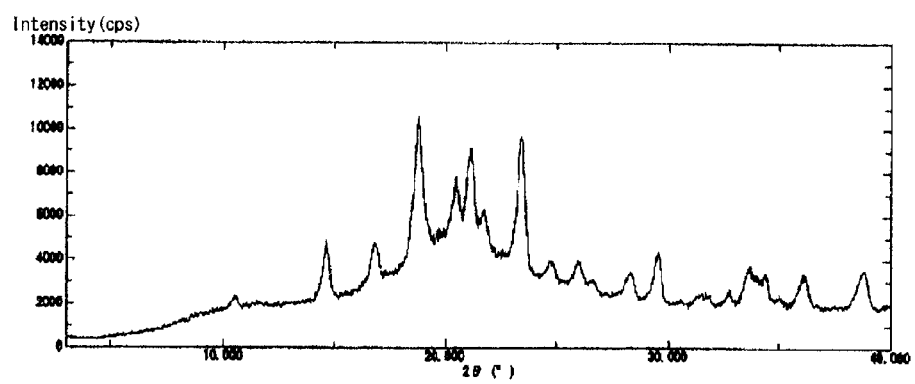
XRD of the 500mg tablet comprising amorphous of the test compound, when made
[Figure 10]
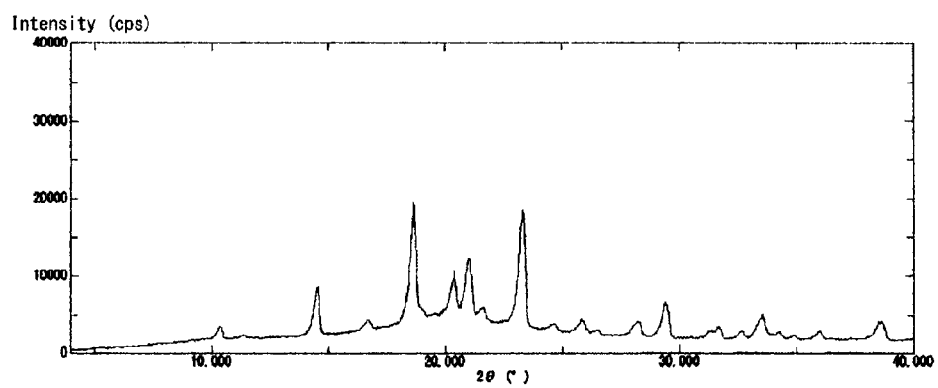
XRD of a powder comprising only a disintegrant, an excipient and a lubricant

[Figure 11]
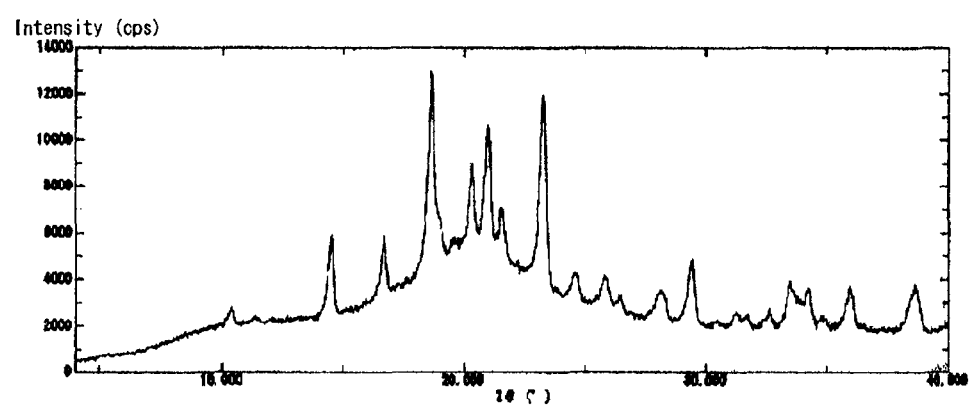
XRD of the 500mg tablet comprising amorphous body composed of the test compound, when sealed and stored for 6 month at 40° C (75%RH)r 6 month at 40° C (75%RH)

AMORPHOUS BODY COMPOSED OF HETEROCYCLIC COMPOUND, SOLID DISPERSION AND PHARMACEUTICAL PREPARATION EACH COMPRISING THE SAME, AND PROCESS FOR PRODUCTION OF THE SAME

TECHNICAL FIELD

The present invention relates to an amorphous body composed of a heterocyclic compound, a solid dispersion and a pharmaceutical preparation comprising the amorphous body, and a method for producing the amorphous body.

BACKGROUND ART

The present inventors have focused on the effects of a s-triazine [1,3,5-triazine] derivative and a pyrimidine derivative substituted with a benzimidazole ring against solid tumors, and have performed research on the synthesis of numerous compounds and the relationship between anti-tumor activities and chemical structures (Patent Documents 1, 2, 3, 4 and 5).

As a result of this research, the present inventors found that a s-triazine derivative and a pyrimidine derivative having a specific substituent at position 2 of the benzimidazole ring such as, for example, 2-(2-difluoromethylbenzimidazol)-4,6-dimorpholino-1,3,5-triazine and others, have an especially strong effect against solid tumors and are effective as anti-tumor agents (Patent Documents 3, 4 and 5).

Furthermore, the present inventors found that these s-triazine and pyrimidine derivatives have an immunosuppressive effect and are effective against disorders that respond to immunosuppressants, such as autoimmune diseases, organ transplantations, allergic diseases, hematological tumors and sepsis (Patent Document 6).

The present inventors have continued to perform research on improvements in order to further increase the efficacy of these heterocyclic compounds (s-triazine and pyrimidine derivatives) as therapeutic agents for various diseases.

Patent Document 1: WO 99/05138
Patent Document 2: WO 00/43385
Patent Document 3: WO 02/088112
Patent Document 4: WO 2004/037812
Patent Document 5: WO 2005/095389
Patent Document 6: WO 2006/095906

DISCLOSURE OF THE INVENTION

Problems to be Solved by the Invention

As a result of performing experiments for further improving the efficacy of s-triazine and pyrimidine derivatives and other heterocyclic compounds, it became clear that these are poorly soluble substances with low bioavailability. The present invention involved an investigation of the problem of providing the above heterocyclic compounds with a high bioavailability.

Means for Solving the Problems

The inventors, as a result of diligent investigations for a method for enhancing the bioavailability, discovered for the first time an amorphous form of the s-triazine and pyrimidine derivatives and a method for the production thereof, and revealed that the amorphous body and a solid dispersion comprising the amorphous body exhibit a high absorbability and stability, which led to the completion of the present invention.

That is, the present invention provides an amorphous body composed of a heterocyclic compound represented by general formula (I):

[Chem. 1]

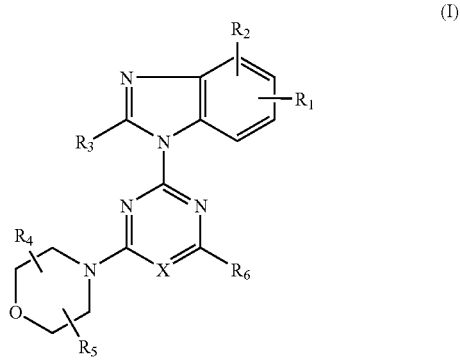

(I)

wherein, X represents a nitrogen atom or CH; $R_1$ and $R_2$, both or either one, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group; $R_3$ represents a hydrogen atom, a difluoromethyl group, an amino group, a $C_1$-$C_6$ alkylamino group, a methyl, or a hydroxymethyl group; $R_4$ and $R_5$ represent a hydrogen atom or a $C_1$-$C_6$ alkyl group; and $R_6$ represents a morpholino (optionally substituted with 1 to 2 $C_1$-$C_6$ alkyl groups), a pyrrolidinyl (optionally substituted with a hydroxy $C_1$-$C_6$ alkyl group), a piperidino (optionally substituted with 1 to 2 oxygen atoms, a hydroxyl group, a formyl, or a $C_1$-$C_6$ alkyl group), a piperazinyl (optionally substituted with 1 to 2 oxygen atoms, the nitrogen at position 4 optionally substituted with a substituent selected from the group consisting of formyl, hydroxyl $C_1$-$C_6$ alkyl, $C_1$-$C_6$ alkoxycarbonyl, oxo $C_1$-$C_6$ alkyl, aromatic carbonyl, benzylcarbonyl and substituted carbamoyl), or a 1,4-diazepano (optionally substituted with 1 to 2 oxygen atoms, the nitrogen at position 4 optionally substituted with a substituent selected from the group consisting of formyl, hydroxy $C_1$-$C_6$ alkyl, $C_1$-$C_6$ alkoxycarbonyl, oxo $C_1$-$C_6$ alkyl, aromatic carbonyl, benzyl carbonyl and substituted carbamoyl); or a hydrate thereof, a solvate thereof, or a pharmaceutically acceptable salt thereof. These amorphous bodies, as compared to the conventional crystals, exhibit high bioavailability, and are therefore especially effective as pharmaceutical preparations.

Moreover, the present invention provides the above amorphous body produced by a spray drying method or a grinding method. By using these processes, the above amorphous body composed of the heterocyclic compound can certainly be obtained.

Moreover, the present invention provides a solid dispersion comprising the above amorphous body and a pharmaceutically acceptable solid polymer. Since in the solid dispersion, the above amorphous body exists in an even more stabilized state, it has an excellent shelf-life etc. and is useful in actual clinical applications.

Moreover, the present invention provides the above solid dispersion, in which the above solid polymer is a cellulose derivative. By using a cellulose derivative as the solid polymer, amorphization and stabilization can proceed more certainly.

Moreover, the present invention provides the above solid dispersion, in which the cellulose derivative is hydroxypropyl cellulose or hypromellose. By using hydroxypropyl cellulose or hypromellose as the solid polymer, amorphization and stabilization can proceed more certainly.

Moreover, the present invention provides the above solid dispersion, in which the mass ratio of the heterocyclic compound, a hydrate thereof, a solvate thereof, or a pharmaceutically acceptable salt thereof and the solid polymer is 1:0.1 to 1:10. By making the solid dispersion at the above mass ratio, amorphization and stabilization can proceed more certainly.

Moreover, the present invention provides the above solid dispersion, in which the above mass ratio is 1:2 to 2.5. By making the solid dispersion at the above mass ratio, amorphization and stabilization can proceed even more certainly.

Moreover, the present invention provides the above solid dispersion, which further comprises an excipient. By including an excipient, the convenience of the solid dispersion as a pharmaceutical preparation, such as stability, is further improved.

Moreover, the present invention provides a formulation, which comprises the above solid dispersion and is provided in the form of a powder, a fine granule, a granule, a tablet or a capsule. By providing the formulation in the form of a powder, a fine granule, a granule, a tablet or a capsule, the convenience of the solid dispersion as a pharmaceutical preparation is further improved.

Moreover, the present invention provides a method for producing an amorphous body composed of a heterocyclic compound represented by general formula (I):

[Chem. 2]

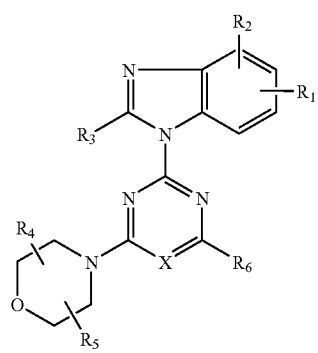

(I)

wherein, X represents a nitrogen atom or CH; $R_1$ and $R_2$, both or either one, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group; $R_3$ represents a hydrogen atom, a difluoromethyl group, an amino group, a $C_1$-$C_6$ alkylamino group, a methyl, or a hydroxymethyl group; $R_4$ and $R_5$ represent a hydrogen atom or a $C_1$-$C_6$ alkyl group; and $R_6$ represents a morpholino (optionally substituted with 1 to 2 $C_1$-$C_6$ alkyl groups), a pyrrolidinyl (optionally substituted with a hydroxy $C_1$-$C_6$ alkyl group), a piperidino (optionally substituted with 1 to 2 oxygen atoms, a hydroxyl group, a formyl, or a $C_1$-$C_6$ alkyl group), a piperazinyl (optionally substituted with 1 to 2 oxygen atoms, the nitrogen at position 4 optionally substituted with a substituent selected from the group consisting of formyl, hydroxyl $C_1$-$C_6$ alkyl, $C_1$-$C_6$ alkoxycarbonyl, oxo $C_1$-$C_6$ alkyl, aromatic carbonyl, benzylcarbonyl and substituted carbamoyl), a 1,4-diazepano (optionally substituted with 1 to 2 oxygen atoms, the nitrogen at position 4 optionally substituted with a substituent selected from the group consisting of formyl, hydroxy $C_1$-$C_6$ alkyl, $C_1$-$C_6$ alkoxycarbonyl, oxo $C_1$-$C_6$ alkyl, aromatic carbonyl, benzyl carbonyl and substituted carbamoyl); or a hydrate thereof, a solvate thereof, or a pharmaceutically acceptable salt thereof; the method comprising a step of dissolving the heterocyclic compound, the hydrate thereof, the solvate thereof or the pharmaceutically acceptable salt thereof in a solvent to prepare a feed solution, a step of spraying the feed solution, and a step of drying the sprayed feed solution to obtain the above amorphous body. According to this method of production, it is possible to produce the above amorphous body more certainly.

EFFECTS OF THE INVENTION

The present invention can increase the bioavailability of the above heterocyclic compound represented by general formula (I), a hydrate thereof, a solvate thereof, or a pharmaceutically acceptable salt thereof.

BRIEF DESCRIPTION OF THE DRAWINGS

FIG. [1] shows a powder X-ray diffraction (XRD) pattern of the test compound crystal.

FIG. [2] shows a powder X-ray diffraction (XRD) pattern of the amorphized test compound. (1 Non-amorphized test compound; 2 Test compound:HPC(SSL)=1:1, spray-dried; 3 Test compound:HPC(SSL)=1:2.5, spray-dried; 4 Test compound:HPC (L)=1:1, spray-dried; 5 Test compound:HPC (L)=1:2.5, spray-dried; 6 Test compound:HPMC=1:2.5, spray-dried; 7 Test compound:PVP=1:1, spray-dried; 8 Test compound:PVP=1:2.5, spray-dried; regarding the spectra of 2 to 8, their heights have been shifted for easier viewing (there is no meaning in the absolute values).)

FIG. [3] is a graph showing the blood concentration of the test compound in rats when the compound was administered at 100 mg/kg.

FIG. [4] are graphs showing the compounding ratio of HPMC with respect to the test compound and blood kinetics of the test compound.

FIG. [5] is a graph showing the blood concentration of the test compound when the preparation, which had been unsealed and stored for a month at 40° C., 75% RH, was administered to rats.

FIG. [6] shows a powder X-ray diffraction (XRD) pattern of the test compound when the amorphous body composed of the test compound was produced.

FIG. [7] shows a powder X-ray diffraction (XRD) pattern of the amorphous body composed of the test compound when the amorphous body had been sealed and stored for a month at 40° C. (75% RH).

FIG. [8] shows a powder X-ray diffraction (XRD) pattern of the amorphous body composed of the test compound when the amorphous body had been unsealed and stored for a month at 40° C. (75% RH).

FIG. [9] shows a powder X-ray diffraction (XRD) pattern of a 500 mg tablet comprising the amorphous body composed of the test compound when the tablet was produced.

FIG. [10] shows a powder X-ray diffraction (XRD) pattern of only a disintegrant, an excipient, and a lubricant.

FIG. [11] shows a powder X-ray diffraction pattern of the 500 mg tablet comprising the amorphous body composed of the test compound when the tablet had been sealed and stored for 6 months at 40° C. (75% RH).

BEST MODES FOR CARRYING OUT THE
INVENTION

The present inventors investigated further improvements of the efficacy of heterocyclic compounds, such as 2-(2-difluoromethylbenzimidazol)-4,6-dimorpholino-1,3,5-triazine and others, and have revealed for the first time that these compounds are poorly soluble substances with low bioavailability. The inventors then investigated the problem of improving the absorbability of these heterocyclic compounds.

An example of general means to improve the bioavailability of poorly soluble compounds is to convert them to a soluble derivative and add a solubilizing agent such as a surfactant during formulation etc. The present inventors, as a result of diligent investigations, discovered an amorphous form of 2-(2-difluoromethylbenzimidazol)-4,6-dimorpholino-1,3,5-triazine that has not been produced, isolated or identified, and revealed, for the first time, a method for producing an amorphous body composed of the compound. Moreover, in addition to the fact that the amorphous body exhibits a high absorbability in animals, the amorphous body was demonstrated to have a good stability, leading to the completion of the present invention.

[Explanation Of Terminology]

The definitions, meanings and examples of all symbols and terms shall be explained as follows:

Regarding the symbols in chemical formulas, they are defined as below.

"$C_1$-$C_6$", unless restricted, means a group having 1 to 6 carbon atoms.

"$C_1$-$C_6$ alkyl" may include, for example, methyl, ethyl, n-propyl, iso-propyl, n-butyl, tert-butyl, n-pentyl, n-hexyl and other linear or branched chain alkyl groups.

"Hydroxy $C_1$-$C_6$ alkyl" means a group in which a hydroxy group is bound to any of the carbon atoms in the above group defined as "$C_1$-$C_6$ alkyl".

"Oxo $C_1$-$C_6$ alkyl" means a group in which an oxo group is bound to any of the carbon atoms in the above group defined as "$C_1$-$C_6$ alkyl".

"$C_1$-$C_6$ alkylamino" means a group in which any atom in the above group defined as "$C_1$-$C_6$ alkyl" is bound to an amino group.

"$C_1$-$C_6$ alkoxy" may include, for example, methoxy, ethoxy, n-propoxy, iso-propoxy, n-butoxy, tert-butoxy, n-pentyloxy, n-hexyloxy and other linear or branched chain alkoxy groups.

"$C_1$-$C_6$ alkoxycarbonyl" means a group in which any atom in the above group defined as "$C_1$-$C_6$ alkoxy" is bound to a carbonyl group.

"Aromatic carbonyl" means a group in which any aromatic group (for example, phenyl, thienyl, furyl or the like) is bound to a carbonyl group.

"Substituted carbamoyl" means a carbamoyl group substituted with an alkyl (for example, the above $C_1$-$C_6$ alkyl etc.) or the above aromatic group, such as methylcarbamoyl, phenylcarbamoyl etc.

The "amorphous body" in the present embodiment refers to substances not comprising a true crystal lattice, is technically similar to vitreous bodies or extremely viscous amorphous liquids, and includes vitreous bodies and viscous amorphous liquids. This kind of amorphous body, as it is clear from its definition, can be clearly identified when compared with a crystalline substance by broadening crystal-specific spectra such as solid-state NMR and diffraction patterns obtained by the (powder) X-ray diffraction (XRD) method and other diffraction methods as well as thermal analysis (differential scanning calorimetry: DSC) etc.

"Spray drying method" is a method of making a solution, slurry, emulsion or the like (feed solution) of a compound into a fine mist, which is blown out in a hot wind or the like to obtain a powdery dried compound. The atomization into a mist may be called "spray", and as methods thereof, centrifugal atomization using a rotating disc and pressure-spraying using a pressure nozzle are well-known.

"Grinding method" is a method of using methods known to those skilled in the art (R. W. Lee et al., Particle Size Reduction in "Water Insoluble Drug Formulation", Rong Liu, Ed., Interpharm Press Co., Denver, Colo.: 473-392 (2000) etc.) to comminute compounds in their solid form. Grinding can be carried out using various devices known in the field such as grinding jars.

"Pharmaceutically acceptable" refers to the property of, not exhibiting excessive toxicities, stimuli, allergic reactions etc., and is suitable to be used in contact with human and animal tissues, within an appropriate range of medical judgment.

"Solid dispersion" refers to a solid composition in which a substance of a solid state is evenly mixed with other substances of a solid state. While in the present embodiment, a solid dispersion, in which the heterocyclic compound according to the present invention is dispersed in the solid polymer, is favorably used, multiple substances may be included as the substance of a solid state, or non-solid components may be included. As long as the composition evenly mixed with the heterocyclic compound takes the solid state, it can be considered to be a solid dispersion.

"Room temperature" or "ordinary temperature" means the general temperature of the outside air. While they respectively represent temperatures of 1 to 40° C. for room temperature and 15 to 28° C. for ordinary temperature, they are not necessarily limited to these temperatures, and when these terms are used, "room temperature" or "ordinary temperature" can be used to indicate normal temperatures.

[Embodiment]

Hereinafter, embodiments of the present invention shall be explained.

An embodiment of the present invention is an amorphous body composed of a heterocyclic compound represented by general formula (I):

[Chem. 3]

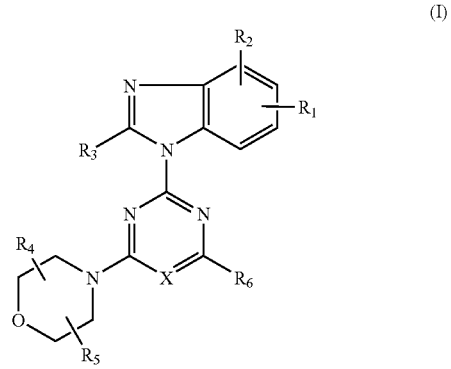

(I)

wherein, X represents a nitrogen atom or CH; $R_1$ and $R_2$, both or either one, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group; $R_3$ represents a hydrogen atom, a difluoromethyl group, an amino group, a $C_1$-$C_6$ alkylamino group, a methyl, or a hydroxymethyl group; $R_4$ and $R_5$ represent a hydrogen atom or a $C_1$-$C_6$ alkyl group; and $R_6$ represents a morpholino (optionally substituted with 1 to 2 $C_1$-$C_6$ alkyl groups), a pyrrolidinyl (optionally substituted with a hydroxy $C_1$-$C_6$ alkyl group), a piperidino (optionally substituted with 1 to 2 oxygen atoms, a hydroxyl group, a formyl, or a $C_1$-$C_6$ alkyl group), a piperazinyl (optionally substituted with 1 to 2 oxygen atoms, the nitrogen at position 4 optionally substituted with a substituent selected from the group consisting of formyl, hydroxyl $C_1$-$C_6$ alkyl, $C_1$-$C_6$ alkoxycarbonyl, oxo $C_1$-$C_6$ alkyl, aromatic carbonyl, benzylcarbonyl and substituted carbamoyl), or a 1,4-diazepano (optionally substituted with 1 to 2 oxygen atoms, the nitrogen at position 4 optionally substituted with a substituent selected from the group consisting of formyl, hydroxy $C_1$-$C_6$ alkyl, $C_1$-$C_6$ alkoxycarbonyl, oxo $C_1$-$C_6$ alkyl, aromatic carbonyl, benzyl carbonyl and substituted carbamoyl); or a hydrate thereof, a solvate thereof, or a pharmaceutically acceptable salt thereof.

Moreover, a further embodiment of the present invention is an amorphous body composed of a heterocyclic compound represented by general formula (II):

[Chem. 4]

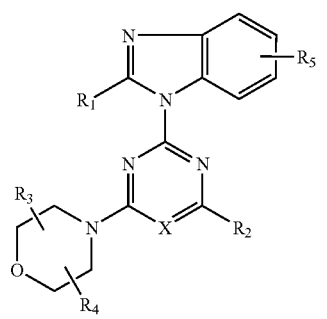

(II)

wherein, X represents a nitrogen atom or CH; $R_1$ represents $CH_nF_{3-n}$ (n is 1 or 2), a hydroxy $C_1$-$C_6$ alkyl, or $NHR_6$ ($R_6$ is a hydrogen atom or COR (R is a hydrogen atom, a $C_1$-$C_6$ alkyl, or a $C_1$-$C_6$ alkoxy)); $R_2$ represents a morpholino (optionally substituted with 1 to 4 $C_1$-$C_6$ alkyl groups), a thiomorpholino, a piperidino, a pyrrolidinyl (optionally substituted with a hydroxyl $C_1$-$C_6$ alkyl), an oxazolidinyl (optionally substituted with 1 to 2 $C_1$-$C_6$ alkyl groups), or tetrahydro-1,4-thiazine-1-oxo-4-yl; $R_3$ and $R_4$ each represents a hydrogen atom or a $C_1$-$C_6$ alkyl; $R_5$ represents a hydrogen atom, an amino or a hydroxyl group; or a hydrate thereof, a solvate thereof, or a pharmaceutically acceptable salt thereof.

These amorphous bodies, when compared to the conventional crystalline forms, exhibit good bioavailability and particularly high intestinal absorbability, and therefore the daily dosage can be decreased and these bodies are effective as pharmaceutical preparations and medicaments. Moreover, they are especially effective as formulations for oral administration. Additionally, by decreasing the variability in absorption among patients, the amorphous bodies can also contribute to reduced variability in plasma concentration among patients, and are therefore beneficial to the improvement of the prediction accuracy of a treatment and homogenization of a treatment.

The heterocyclic compound of the above formula (I) includes, but is not limited to, for example, the following compounds:

The above heterocyclic compound in which either $R_1$ or $R_2$ is a hydroxyl group.

The above heterocyclic compound in which either $R_1$ or $R_2$ is a hydroxyl group, and $R_3$ is a difluoromethyl.

The above heterocyclic compound in which both $R_1$ and $R_2$ are hydrogen atoms, and $R_3$ is a difluoromethyl.

The above heterocyclic compound in which $R_6$ is 4-acetylpiperazine.

The heterocyclic compound of the above formula (II) includes, but is not limited to, for example, the following compounds:

The above heterocyclic compound in which $R_1$ is a difluoromethyl.

The above heterocyclic compound in which $R_1$ is a difluoromethyl, $R_2$ is a morpholino that is optionally substituted with 1 to 3 methyl groups, $R_3$ and $R_4$ are each a hydrogen atom or a methyl.

The above heterocyclic compound in which $R_1$ is a difluoromethyl, $R_2$ is a morpholino that is optionally substituted with 1 to 3 methyl groups, $R_3$ and $R_4$ are hydrogen atoms, and $R_5$ is an amino or a hydroxyl group.

The above heterocyclic compound in which $R_1$ is a hydroxymethyl.

The above heterocyclic compound in which $R_1$ is a hydroxymethyl, $R_2$ is a morpholino that is optionally substituted with 1 to 2 methyl groups, $R_3$ and $R_4$ are each a hydrogen atom or a methyl.

The above heterocyclic compound in which $R_1$ is an amino, a formylamino, or an acetylamino.

The above heterocyclic compound in which $R_1$ is an amino, a formylamino, or an acetylamino, $R_2$ is a morpholino that is optionally substituted with 1 to 2 methyl groups, $R_3$ and $R_4$ are each a hydrogen atom.

Furthermore, the heterocyclic compound of the above formula (I) or formula (II) includes, but is not limited to, for example, the following compounds:

2-(2-difluoromethylbenzimidazol-1-yl)-4-(cis-2,3-dimethylmorpholino)-6-morpholinopyrimidine 2-(2-difluoromethylbenzimidazol-1-yl)-4,6-dimorpholinopyrimidine 2-(2-difluoromethylbenzimidazol-1-yl)-4-morpholino-6-thiomorpholinopyrimidine 2-(2-difluoromethylbenzimidazol-1-yl)-4-(trans-2,3-dimethylmorpholino)-6-morpholinopyrimidine 2-(2-difluoromethylbenzimidazol-1-yl)-4-(2,2-dimethylmorpholino)-6-morpholinopyrimidine 2-(2-difluoromethylbenzimidazol-1-yl)-4-(2-methylmorpholino)-6-morpholinopyrimidine 2-(2-difluoromethylbenzimidazol-1-yl)-4-morpholino-6-[2,2,5(R)-trimethylmorpholino]pyrimidine 2-(2-difluoromethylbenzimidazol-1-yl)-4-morpholino-6-[2,2,5(S)-trimethylmorpholino]pyrimidine 4-(cis-2,3-dimethylmorpholino)-2-(2-fluoromethylbenzimidazol-1-yl)-6-morpholinopyrimidine 2-(2-aminobenzimidazol-1-yl)-4-(cis-2,3-dimethylmorpholino)-6-morpholinopyrimidine 2-(2-aminobenzimidazol-1-yl)-4-(trans-2,3-dimethylmorpholino)-6-morpholinopyrimidine 4-(cis-2,3-dimethylmorpholino)-2-(2-hydroxymethylbenzimidazol-1-yl)-6-morpholinopyrimidine 4-(cis-2,3-dimethylmorpholino)-2-(2-hydroxymethylbenzimidazol-1-yl)-6-piperidinopyrimidine 4-(cis-2,3-dimethylmorpholino)-2-(2-hydroxymethylbenzimidazol-1-yl)-6-(2-hydroxymethylpyrrolidin-1-yl)pyrimidine
2-(6-amino-2-difluoromethylbenzimidazol-1-yl)-4,6-dimorpholinopyrimidine
2-(6-amino-2-difluoromethylbenzimidazol-1-yl)-4-(cis-2,3-dimethylmorpholino)-6-morpholinopyrimidine
2-(2-difluoromethyl-5-hydroxybenzimidazol-1-yl)-4,6-dimorpholinopyrimidine
2-(2-difluoromethyl-4-hydroxybenzimidazol-1-yl)-4-(2,2-dimethylmorpholino)-6-morpholinopyrimidine
2-(2,4-diaminobenzimidazol-1-yl)-4-(2,2-dimethylmorpholino)-6-morpholinopyrimidine
2-(2,4-diaminobenzimidazol-1-yl)-4,6-dimorpholinopyrimidine
2-(2-amino-4-hydroxybenzimidazol-1-yl)-4-(2,2-dimethylmorpholino)-6-morpholinopyrimidine
2-(2-difluoromethylbenzimidazol-1-yl)-4-(cis-2,3-dimethylmorpholino)-6-morpholino-1,3,5-triazine
2-(2-difluoromethylbenzimidazol-1-yl)-4-(trans-2,3-dimethylmorpholino)-6-morpholino-1,3,5-triazine
2-(2-difluoromethylbenzimidazol-1-yl)-4-(2,2-dimethylmorpholino)-6-morpholino-1,3,5-triazine
2-(2-difluoromethylbenzimidazol-1-yl)-4-morpholino-6-thiomorpholino-1,3,5-triazine
2-(2-difluoromethylbenzimidazol-1-yl)-4-(2-methylmorpholino)-6-morpholino-1,3,5-triazine
2-(2-difluoromethylbenzimidazol-1-yl)-4-(trans-2,5-dimethylmorpholino)-6-morpholino-1,3,5-triazine
2-(2-difluoromethylbenzimidazol-1-yl)-4,6-dimorpholino-1,3,5-triazine
2-(2-difluoromethylbenzimidazol-1-yl)-4-morpholino-6-[2,2,5(R)-trimethylmorpholino]-1,3,5-triazine
2-(2-difluoromethylbenzimidazol-1-yl)-4-morpholino-6-(tetrahydro-1,4-thiazin-1-oxo-4-yl)-1,3,5-triazine
2-(2-acetylaminobenzimidazol-1-yl)-4,6-dimorpholino-1,3,5-triazine
2-(2-acetylaminobenzimidazol-1-yl)-4-(trans-2,3-dimethylmorpholino)-6-morpholinopyrimidine
2-(2-formylaminobenzimidazol-1-yl)-4,6-dimorpholino-1,3,5-triazine
2-(2-propionylaminobenzimidazol-1-yl)-4-(trans-2,3-dimethylmorpholino)-6-morpholino-1,3,5-triazine
2-(trans-2,3-dimethylmorpholino)-4-(2-formylaminobenzimidazol-1-yl)-6-morpholino-1,3,5-triazine
4-(trans-2,3-dimethylmorpholino)-2-(2-formylaminobenzimidazol-1-yl)-6-morpholinopyrimidine
2-(cis-2,6-dimethylmorpholino)-4-(2-formylaminobenzimidazol-1-yl)-6-morpholino-1,3,5-triazine
2-(2-methoxycarbonylaminobenzimidazol-1-yl)-4,6-dimorpholino-1,3,5-triazine
2-(2-aminobenzimidazol-1-yl)-4,6-dimorpholino-1,3,5-triazine
2-(2-aminobenzimidazol-1-yl)-4-(trans-2,3-dimethylmorpholino)-6-morpholino-1,3,5-triazine
2-(2-aminobenzimidazol-1-yl)-4-(cis-2,3-dimethylmorpholino)-6-piperidino-1,3,5-triazine
2-(2-difluoromethylbenzimidazol-1-yl)-4-morpholino-6-piperidino-1,3,5-triazine
2-(2-difluoromethylbenzimidazol-1-yl)-4-(trans-2,3-dimethylmorpholino)-6-(2-hydroxymethylpyrrolidin-1-yl)-1,3,5-triazine
2-(6-amino-2-difluoromethylbenzimidazol-1-yl)-4-(2,2-dimethylmorpholino)-6-morpholino-1,3,5-triazine
2-(6-amino-2-difluoromethylbenzimidazol-1-yl)-4-(cis-2,3-dimethylmorpholino)-6-morpholino-1,3,5-triazine
2-(4-amino-2-difluoromethylbenzimidazol-1-yl)-4,6-dimorpholino-1,3,5-triazine
2-(2-difluoromethyl-5-hydroxybenzimidazol-1-yl)-4-(2,3-cis-dimethylmorpholino)-6-morpholino-1,3,5-triazine
2-(2-difluoromethyl-6-hydroxybenzimidazol-1-yl)-4-(2,2-dimethylmorpholino)-6-morpholino-1,3,5-triazine
2-(2-difluoromethyl-5-hydroxybenzimidazol-1-yl)-4-(2,2-dimethyloxazolidin-3-yl)-6-morpholino-1,3,5-triazine
2-(2-difluoromethyl-4-hydroxybenzimidazol-1-yl)-4,6-dimorpholino-1,3,5-triazine
2-(2-difluoromethyl-4-hydroxybenzimidazol-1-yl)-4-(2,2-dimethylmorpholino)-6-morpholino-1,3,5-triazine
2-(2,4-diaminobenzimidazol-1-yl)-4-(2,2-dimethylmorpholino)-6-morpholino-1,3,5-triazine
2-(2,4-diaminobenzimidazol-1-yl)-4,6-dimorpholino-1,3,5-triazine
2-(2-amino-4-hydroxybenzimidazol-1-yl)-4-(2,2-dimethylmorpholino)-6-morpholino-1,3,5-triazine Additionally, among the above compounds, 2-(2-difluoromethylbenzimidazol-1-yl)-4,6-dimorpholino-1,3,5-triazine shall be referred to as the test compound in the present specification.

Those skilled in the art would be able to synthesize the above heterocyclic compounds by combining various known reactions (see, for example, Patent Documents 1-6). For example, 2-(2-difluoromethylbenzimidazol-1-yl)-4,6-dimorpholino-1,3,5-triazine can be synthesized by following the methods described in the examples of Patent Document 3.

When the above heterocyclic compounds have an asymmetric carbon atom in their structure, isomers derived from the asymmetric carbon atoms and mixtures thereof (racemic form) are also included.

Furthermore, the above heterocyclic compounds may take the forms of a hydrate, a solvate or an acid addition salt as a pharmacologically acceptable salt etc.

An appropriate solvate may include, for example, an organic solvate such as a dimethyl sulfoxide solvate, a dimethyl amide solvate, and an alcohol solvate such as an ethanol solvate, a methanol solvate, and a n-propyl solvate. An appropriate acid addition salt may include an inorganic acid salt, for example, a hydrochloride, a sulfate, a hydrobromide, a nitrate, and a phosphate etc.; and an organic salt, for example, an acetate, an oxalate, a propionate, a glycolate, a lactate, a pyruvate, a malonate, a succinate, a maleate, a fumarate, a malate, a tartrate, a citrate, a benzoate, a cinnamate, a methane sulfonate, a benzene sulfonate, a p-toluene sulfonate and a salicylate etc.

While many amorphous bodies are known to quickly crystallize and have poor stability, it became clear that the amorphous body of the present invention does not easily crystallize or decompose and is a stable amorphous body. Since the amorphous body of the present invention is superior in its stability and has a higher bioavailability than a crystalline pharmaceutical preparation, it is also useful in the manufacture and supply of substances maintained at a certain quality as medicaments, as well as the uses thereof.

While the above amorphous body can be identified using known art such as differential scanning calorimetry (DSC), solid-state NMR and X-ray diffraction (XRD), the techniques are not restricted, and any techniques capable of verifying amorphous forms may be used to identify the amorphous bodies.

When using XRD, in contrast to a crystalline form, which shows a spectrum containing sharp peaks, an amorphous body shows a spectrum containing relatively broad and weak peaks (broad peaks) with respect to the width of a baseline spectrum, and therefore it is possible to distinguish the forms easily. As an example, it is possible to distinguish the crystalline form and amorphous form of 2-(2-difluoromethylbenzimidazol)-4,6-dimorpholino-1,3,5-triazine by the presence of distinguishing characteristic peaks at diffraction angles 2θ=5 to 14, and particularly 2θ=7 to 10.

When performing differential scanning calorimetry, various DSC temperature recording graphs including a TA Differential Scanning Calorimeter, nitrogen gas as the purge gas, rate of temperature increase at 5° C./min., other devices and conditions etc. can be used. A crystalline body, in general, is characterized by a sharp fusion endothermic/endothermic peak, and while an amorphous body can be distinguished by the lack of the specific endothermic peak seen in a crystalline body, those skilled in the art would be able to identify the presence of an amorphous body from a comparison of DSC temperature recording graphs of a crystalline body and an amorphous body.

While the above amorphous body, its method of production being not restricted, can be produced by using commonly employed methods for producing amorphous bodies such as the freeze drying method, spray drying method, grinding (mixed grinding) method, supercritical fluid method, solvent method and fusion method etc., it is more preferably produced using the spray drying method or the grinding method.

The spray drying method and the grinding method can both be performed by following common procedures. When the spray drying method is used, a stabilized and homogeneous amorphous body can be obtained with good reproducibility, and is advantageous for the production and supply of substances maintained at a certain quality as medicaments. Moreover, when the grinding method is used, grain refinement can be actively performed along with the amorphization, and is advantageous for bioavailability. For the grinding method, a mixed grinding method, in which the compound is ground with a solid polymer (solid base) or the like, can be used. Furthermore, methods for producing a solid dispersion in which a poorly-soluble drug and a water-soluble polymer base are processed without heating by a mixed grinding method (mechanochemical method) such as mixed grinding by a ball mill or roll mixing to amorphize the poorly soluble drug may also be included. Mechanochemical refers to a phenomenon in which mechanical energy (compression, shearing and friction) causes changes in the physicochemical property of a substance, and it is thought that with this method, various factors such as mechanical operation-induced lattice defects, lattice mismatches and increases in specific surface area and surface energy would improve the activity of a solid substance to promote the amorphization of a drug as well as the dispersion of the amorphized drug in a carrier.

The solvent method is a method for producing a solid dispersion by either dissolving a drug and a water-soluble polymer base, which is the carrier, in an organic solvent that dissolves both and then removing the solvent, or dissolving the drug in an organic solvent, dispersing it in the carrier, and then removing the solvent.

For the fusion method, there is a method of obtaining a solid dispersion by using melting point depression of a drug and a water-soluble polymer carrier to heat and melt both substances, then cooling, solidifying and grinding the melted substances [*Chem. Pharm. Bull*, 9, 866 (1961)], and there is a method of obtaining a solid dispersion by heat dissolving a drug in a water-soluble polymer with a relatively low melting point, then cooling, solidifying and grinding the mixture [*Int. J. Pharm*, 47, 51 (1988)].

An example of the above spray drying method is, for example, a method for producing an amorphous body composed of a heterocyclic compound represented by general formula (I):

[Chem. 5]

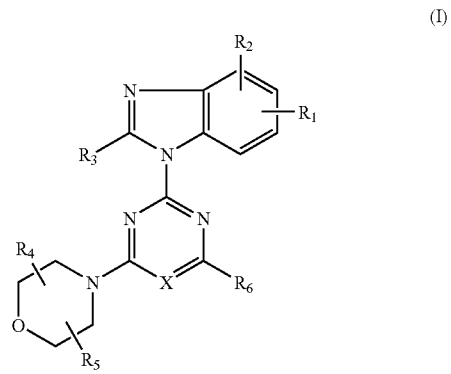

(I)

wherein, X represents a nitrogen atom or CH; $R_1$ and $R_2$, both or either one, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group; $R_3$ represents a hydrogen atom, a difluoromethyl group, an amino group, a $C_1$-$C_6$ alkylamino group, a methyl, or a hydroxymethyl group; $R_4$ and $R_5$ represent a hydrogen atom or a $C_1$-$C_6$ alkyl group; and $R_6$ represents a morpholino (optionally substituted with 1 to 2 $C_1$-$C_6$ alkyl groups), a pyrrolidinyl (optionally substituted with a hydroxy $C_1$-$C_6$ alkyl group), a piperidino (optionally substituted with 1 to 2 oxygen atoms, a hydroxyl group, a formyl, or a $C_1$-$C_6$ alkyl group), a piperazinyl (optionally substituted with 1 to 2 oxygen atoms, the nitrogen at position 4 optionally substituted with a substituent selected from the group consisting of formyl, hydroxyl $C_1$-$C_6$ alkyl, $C_1$-$C_6$ alkoxycarbonyl, oxo $C_1$-$C_6$ alkyl, aromatic carbonyl, benzylcarbonyl and substituted carbamoyl), or a 1,4-diazepano (optionally substituted with 1 to 2 oxygen atoms, the nitrogen at position 4 optionally substituted with a substituent selected from the group consisting of formyl, hydroxy $C_1$-$C_6$ alkyl, $C_1$-$C_6$ alkoxycarbonyl, oxo $C_1$-$C_6$ alkyl, aromatic carbonyl, benzyl carbonyl and substituted carbamoyl); or a hydrate thereof, a solvate thereof, or a pharmaceutically acceptable salt thereof; the method comprising a step of dissolving the heterocyclic compound, the hydrate thereof, the solvate thereof or the pharmaceutically acceptable salt thereof in a solvent to prepare a feed solution, a step of spraying the feed solution, and a step of drying the sprayed feed solution to obtain the amorphous body.

Naturally, the heterocyclic compound of formula (II) can also be produced by the same method.

As a solvent used in the spray drying method, while any solvents capable of dissolving the above heterocyclic compound, the hydrate thereof, the solvate thereof or the pharmaceutically acceptable salt thereof can be used, an organic solvent is preferred. Specifically, the solvent may include a lower alcohol such as methanol, ethanol and isopropanol; a ketone such as acetone and methyl ethyl ketone; a halogenated hydrocarbon such as methylene chloride, dichloroethane, chloroform and carbon tetrachloride; an ether such as diethyl ether; a mixed solvent of these solvents or the like; however, the solvent is not limited to these. These solvents can be used by further adding purified water or an aqueous buffer. Even among these organic solvents, a mixed solvent of a lower alcohol and a halogenated hydrocarbon is preferred from the aspects of solubility and removal afterwards, and a mixed solvent of methanol or ethanol and methylene chloride is further preferred. As for the aqueous buffer, a buffer adjusted to a desired pH containing, for example, citric acid, ethylenediaminetetraacetate (EDTA) or sodium lauryl sulfate (SLS) etc. may be used. Moreover, the feed solution may further contain a solid base such as a solid polymer or other pharmaceutically acceptable components.

Moreover, the above spray drying method may further include a step of heating the feed solution, and heating may be performed when spraying the feed solution or when drying the sprayed feed solution. The temperature used for heating depends on the used dissolving solvent or the compound contained therein, and is determined from among temperatures that do not promote the decomposition of the contained compound (amorphous body), or lower temperatures. For example, the temperature at least 20° C. or above, 30 to 100° C., or 40 to 80° C. can be used; however, the temperature is not limited to these.

Moreover, when drying, pressure reduction may be further performed. The pressure at this step is preferably a reduced pressure having a pressure less than 1 atmospheric pressure (1013.25 hPa); however, the pressure is not limited to this.

The device for carrying out the above grinding method may include, for example, a grinding jar, a ball mill, and a fluid energy mill etc., and those skilled in the art would be able to determine the grinding device and conditions (grinding time and temperature etc.) by following common procedures.

Moreover, another embodiment of the present invention is a solid dispersion comprising the above amorphous body and a pharmaceutically acceptable solid polymer. Since in the solid dispersion, the amorphous body composed of the above heterocyclic compound, the hydrate thereof, the solvate thereof or the pharmaceutically acceptable salt thereof exists stably, utility in storage and actual clinical application become higher.

This type of solid dispersion can be prepared by following common procedures, and although the method for producing the solid dispersion is not restricted, the solid dispersion may be preferably obtained by a spray drying method in which a solid polymer, which is the solid base, is contained in the feed solution, or by a mixed grinding method.

The solid polymer used in the above solid dispersion is a pharmaceutically acceptable substance that is not particularly restricted as long as it can keep the amorphous state of the contained heterocyclic compound, and it may be used alone or as a mixture of two or more solid polymers. Preferably, a water-soluble or a water-insoluble solid polymer that is solid at room temperature is used.

The above solid polymer may include, for example, a cellulose derivative such as hypromellose (HPMC), hydroxypropyl cellulose (HPC), hypromellose phthalate (HPMCP), hydroxypropyl methylcellulose acetate, hydroxypropyl methylcellulose acetate succinate cellulose (HPMCAS), ethyl cellulose, hydroxyethyl cellulose, methyl cellulose, carmellose (CMC), carmellose sodium (CMC-Na), carmellose calcium (CMC-Ca), croscarmellose sodium and low-substituted hydroxypropyl cellulose (L-HPC); povidone (PVP), crospovidone, a methacrylate copolymer, polyethylene glycol (PEG), polyvinyl alcohol (PVA), polyvinyl acetate phthalate, polyvinylacetal diethylaminoacetate, cellulose acetate phthalate, methylcellulose acetate phthalate, sodium carboxymethyl starch, any kind of starch, a partially pregelatinized starch, pectin, pullulan, mannan, gelatin, gum arabic, a dextrin, a cyclodextrin, agar, a polyoxysorbitan fatty acid ester and an alginate.

Here, when the proportion of the solid polymer is too low with respect to the above heterocyclic compound, the hydrate thereof, the solvate thereof, or the pharmaceutically acceptable salt thereof, amorphization becomes difficult, and when the proportion is high, the stability of the amorphous body is better, though there are cases where the bioavailability is affected. The mass ratio of the heterocyclic compound, the hydrate thereof, the solvate thereof, or the pharmaceutically acceptable salt thereof to the solid polymer is preferably 1:0.1 to 10, more preferably 1:1 to 5, and most preferably 1:2 to 2.5; however, the ratio is not restricted to these.

Moreover, another embodiment of the present invention is a formulation, which comprises the above solid dispersion and is provided in the form of a powder, a fine granule, a granule, a tablet or a capsule. By providing the formulation in the form of a powder, a fine granule, a granule, a tablet or a capsule, the convenience of the solid dispersion as a formulation for oral administration is further improved. One of the preferred embodiments is a solid dispersion or a formulation, particularly a formulation for oral administration, comprising an excipient.

The amorphous body, solid dispersion and formulation of the present invention can be administered orally or parenterally, and a powder, a fine granule, a granule, a tablet or a capsule can be suitably used as the dosage form for oral administration. Moreover, a suppository can be suitably used as the dosage form for parenteral administration. Furthermore, the amorphous body, solid dispersion and formulation of the present invention can also be dispersed in a pharmaceutically acceptable solution in advance and be used as a liquid formulation, and in this case, they can be used as a syrup or an injectable formulation for parenteral administration (including lyophilized forms for injection that are dissolved when used). Moreover, it is possible to prepare them as a liposome formulation. In the preparation of these dosage forms, a commonly used coloring, sweetener, flavoring agent, diluent, excipient, binding agent, lubricant, disintegrant, softening agent, suspending agent, emulsifying agent, preservative, anti-oxidant, surfactant, stabilizing agent, pH adjusting agent, and dispersing agent can be used. Moreover, depending on the conditions of use, a functional coating such as an enteric coating may be further applied to these dosage forms. Each of these dosage forms can be prepared by following common procedures and may be prepared aseptically.

For example, the disintegrant may be gum Arabic, a starch (corn starch, potato starch, wheat starch, rice starch etc.), agar, tragacanth, crystalline cellulose, low-substituted hydroxypropyl cellulose, croscarmellose sodium, carmellose calcium, carmellose sodium, and sodium carboxymethyl starch etc.

Moreover, the excipient may be a crystalline cellulose, a sugar (glucose, sucrose, lactose, D-mannitol, and D-sorbitol etc.), a starch (corn starch, potato starch, wheat starch and rice starch), magnesium silicate, sodium hydrogen phosphate, calcium hydrogen phosphate and talc etc.

The lubricant may be carnauba wax, a hydrogenated oil, magnesium stearate, calcium stearate, sodium hydrogen phosphate, calcium hydrogen phosphate and bleached beeswax etc.

Moreover, the solid dispersion or formulation of the present invention may partially comprise the crystalline form of the above heterocyclic compound, the hydrate thereof, the solvate thereof, or the pharmaceutically acceptable salt thereof. It is preferred, though not limited, for at least 75% of the above heterocyclic compound, the hydrate thereof, the solvate thereof, or the pharmaceutically acceptable salt thereof to exist in the amorphous form in the solid dispersion or formulation. It is further preferred that this amount be at least 90%, 95% or 99%. It is most preferred for 100% of the above heterocyclic compound, the hydrate thereof, the solvate thereof of the pharmaceutically acceptable salt thereof to be in the amorphous form in the solid dispersion or formulation. The proportion of the amorphous body present can be determined by, for example, comparing the spectra of solid-state NMR etc. of a crystalline body and an amorphous body etc.

When the amorphous body, solid dispersion and formulation of the present invention are applied to a mammal, especially a human, any dosage forms suitable for the desired route of delivery may be used, and while it is possible to deliver them via, for example, routes such as oral, cutaneous, intracutaneous, intrabronchial, intranasal, intravenous, intramuscular, subcutaneous, parenteral, intraperitoneal, intranasal, vaginal, rectal, sublingual, intracranial, intradural and intratracheal, oral administration is preferred.

The pharmaceutically effective dosage of the amorphous body, solid dispersion and formulation of the present invention may vary depending on the compound, delivery format, seriousness of the disease to be treated and other components. They can be delivered daily in divided doses (for example, a 1-day dose divided into 2 to 4 doses), or they can be delivered in a single dose. Moreover, the delivery may be on a daily, weekly or monthly basis.

The target disorders of the amorphous body, solid dispersion and formulation of the present invention include, but are not limited to, for example, solid tumors including sarcomas and carcinomas such as small cell lung cancer, non-small cell lung cancer, colon cancer, prostate cancer, skin cancer, melanoma, osteosarcoma, liver cancer, hepatocellular carcinoma, kidney cancer, nerve tumor, osteosarcoma, cervical cancer, endometrial cancer, breast cancer and ovarian cancer etc; and hematological neoplasms such as fibrosis, malignant lymphoma, multiple myeloma, chronic leukemia, acute leukemia, myeloid leukemia etc.

Moreover, the amorphous body, solid dispersion and formulation of the present invention may be used for autoimmune diseases such as rheumatoid arthritis, systemic lupus erythematosis, scleroderma, and Sjögren's syndrome etc.; organ dysfunctions accompanying autoimmune diseases such as uveitis, glomerulonephritis, thyroiditis, pancreatitis and bone destruction etc.; rejection response during tissue transplantation and graft-versus-host disease during bone marrow transplantation; inflammatory bowel diseases such as ulcerative colitis and Crohn's disease; inflammatory or allergic skin diseases such as psoriasis and atopic dermatitis; inflammatory or allergic respiratory diseases such as chronic obstructive pulmonary disease and asthma; allergic conjunctivitis and rhinitis; hematological neoplasms originating from cells of the immune system such as B-lymphoma, T-lymphoma and myeloid leukemia; diseases induced by infection of gram-negative bacteria or coronaviruses such as sepsis, severe acute respiratory syndrome and fulminant hepatitis.

An appropriate dosing regime can be determined based on common knowledge in the art, information provided by the present specification and experience with respect to each subject being treated. Usually, it is preferred that the amorphous body, solid dispersion and formulation of the present invention are administered at a concentration that produces effective results without inducing dangerous or adverse side-effects.

As an example, when used as an oral formulation, the dose of the effective ingredient differs depending on the symptoms, age and body weight etc. of the patient; however, for an adult with a body weight of 60 kg, a daily dose of 10 to 500 mg can be separated and given in 2 to 3 administrations. Moreover, when eye drops, inhalation into the lung or nasal cavity, or injection into the inflamed joint space is the purpose, the dosage will also differ depending on the symptoms of the patient; however, for an adult, a daily dose of 1 to 100 µg can be separated and given in 2 to 3 administrations.

EXAMPLES

Hereinafter, the present invention shall be specifically explained using examples; however, each of these is only an example and the present invention is not limited to them. Additionally, unless specifically indicated, the commercially available reagents, machines and devices mentioned in the examples were used according to the manufacturers' instructions or common procedures.

Moreover, the test compound (2-(2-difluoromethylbenzimidazol)-4,6-dimorpholino-1,3,5-triazine) was synthesized according to the method described in the examples of Patent Document 3.

The present inventors carried out the screening of the test compound (2-(2-difluoromethylbenzimidazol)-4,6-dimorpholino-1,3,5-triazine), which is one of the heterocyclic compounds according to the present invention by preparing it using an agate mortar and suspending it in a hydroxypropyl cellulose (HPC) aqueous solution; however, it was clear at the time that the blood kinetics remarkably differed with each production lot. Using blood kinetic parameters of drugs in rats as indicators, various examinations were performed in order to obtain a formula by which a homogeneous formulation with superior blood kinetics can be produced.

In general, since it is known that the grain refinement of a drug improves its bioavailability, grain refinement was attempted using a jet mill, a microfluidizer or an agitation mill. As a result, although grain refinement was achieved, an improvement in the bioavailability was not observed in experiments using rats.

Next, for mixtures of the test compound with HPC or with hypromellose (HPMC), mixed grinding by air flow mixing was attempted. With this mixed grinding, partial amorphization of the test compound was observed and an improvement in the bioavailability was noticed. Further, when the spray drying method was investigated, an almost complete amorphization of the test compound was observed, and a dramatic improvement in the bioavailability was seen. The content of the amorphous form of the test compound correlated with the improvement in absorbability, and the amorphous form of the test compound, when compared to the crystallized form, was confirmed to have an extremely high absorbability.

Next, further investigations were performed on the amorphous form of the test compound. In general, it is difficult for the amorphous form of certain compounds to maintain the amorphized state, and the amorphous form is known to gradually crystallize with the passage of time. When the amorphous body composed of the test compound prepared by the spray drying method was investigated, it was clear that this amorphous body is stable for a long period of time at ordinary temperature.

As described above, the present inventors discovered the amorphous form of the test compound for the first time and elucidated the method for producing the amorphous body. Moreover, the amorphous body improved the problem of the poor absorption rate of the test compound. Further, the amorphous body was stable for a long period of time at ordinary temperature. Based on these findings, it was clear that the amorphous form of the test compound is extremely effective as a pharmaceutical preparation, especially as a formulation in a dosage form that is prone to have a problem with bioavailability, such as a formulation for oral administration.

Details of each experiment are shown below.

Example 1

Preparation of an Amorphous Body of the Test Compound by a Spray Drying Method 121.6 g of methylene chloride and 30.4 g of methanol were placed in a 300 mL-volume Erlenmeyer flask. The test compound and HPC were dissolved in the flask to prepare a 5% test compound solution. The heat input temperature was controlled so as to keep the exhaust heat temperature around 60° C., and the feed solution was sprayed while maintaining a constant spray pressure. The obtained preparation was dried under reduced pressure overnight at room temperature using a laboratory vacuum dryer.

Example 2

Preparation of an Amorphous Body of the Test Compound by a Spray Drying Method

Using the same method as Example 1, the process was carried out with HPC changed to PVP or HPMC. The process was performed at ratios of 1:1.5, 1:2.0, 1:2.5 and 1:5 of the test compound to these solid polymers.

Example 3

Analysis of an Amorphous Body of the Test Compound by an X-Ray Diffraction (XRD) Method When a crystal of the test compound obtained by common procedures was analyzed using the powder X-ray diffraction method, several characteristic peaks at diffraction angles $2\theta=5$ to 14, and especially at $2\theta=7$ to 10, were observed (FIG. 1). In contrast, when the preparations obtained in Examples 1 and 2 were analyzed using the powder X-ray diffraction (XRD) method, the peaks at diffraction angles characteristic to a crystalline form were not observed, and it was clear that the test compound was in an amorphized state in these preparations (FIG. 2).

Example 4

Preparation of an Amorphous Body of the Test Compound by a Mixed Grinding Method 0.75 g of the test compound and HPMC were each weighed out and mixed ground for 2 hours in an Ishikawa-type agitating grinder (AGA-type, Ishikawa Kojo).

Example 5

Preparation of an Amorphous Body of the Test Compound by a Mixed Grinding Method Using the same method as Example 3, mixed grinding was carried out with HPMC changed to HPC, PVP or D-mannitol.

Example 6

Preparation of an Amorphous Body of the Test Compound by a Solvent Removal Method 2.4 g of the test compound and 6.0 g of HPC (L) were weighed out and dissolved in 300 mL of methylene chloride. The organic solvent was removed under reduced pressure using an evaporator and a solid dispersion of the test compound was obtained.

Example 7

Blood Concentration Measurement for Each Administration of the Test Compound Samples 7-week old SD male rats were purchased from Charles River Laboratories Japan (Inc.), preliminarily kept for a week and then used for experiments. Fasting began 16 hours before drug administration, and each of the preparations obtained from Examples 1, 4 and 5, when used, was mixed with distilled water to make a 100 mg/5 ml/kg test compound suspension, which was administered orally. Blood was sequentially collected from the tail vein using heparin-treated glass blood collection tubes from 15 min. to 24 or 30 hours after the administration of these preparations, centrifuged (3,000 rpm, 10 min., 4° C.) to obtain plasma, and the blood concentration of the test compound was evaluated (FIG. 3).

As a result, compared to the control bulk drug substance in crystalline form, a high blood concentration of the test compound was observed for all the preparations containing the test compound in amorphous form, and it was clear that these amorphous bodies improved the absorbability from the intestinal tract. In particular, the solid dispersions obtained by the spray drying method or mixed grinding method had remarkable effects, and the solid dispersion produced by the spray drying method with HPMC demonstrated the highest absorbability. Further, when the area under the curve (AUC24) of the blood concentration and the maximum blood concentration ($C_{max}$) up to 24 hours post-administration were evaluated with the compounding ratio of the test compound and HPMC, the results demonstrated that 1 to 5 HPMC against 1 test compound was desirable, and 2 to 2.5 was the optimal compounding ratio (FIG. 4).

Example 8

Changes in the State of the Amorphous Body of the Test Compound after a Long Period of Time In order to investigate the changes in the state of an amorphous body of the test compound, a solid dispersion produced by the spray drying method with a 1:2.5 test compound to HPMC compounding ratio was stored under certain conditions, and changes in the state of the amorphous body of the test compound were analyzed by powder X-ray diffraction similar to Example 3. The results are shown in Table 1. As a result, when the solid dispersion was stored in a hermetically sealed state in a sealed glass container, peaks at diffraction angles demonstrating crystallization could not be identified even after 6 months of storage at 25° C. or 40° C., and it was clear that the amorphous body of the test compound is sufficiently stable when used as a pharmaceutical preparation.

TABLE 1

| Storage Temperature (° C.) | Storage Condition | Storage Period (months) | | | |
|---|---|---|---|---|---|
| | | 0.5 | 1 | 3 | 6 |
| 25 | Sealed | — | ○ | ○ | ○ |
| 40 | Unsealed (75% RH) | X | X | — | — |
| | Sealed | ○ | ○ | ○ | ○ |
| 60 | Sealed | Δ | Δ | — | — |

○: no peaks at diffraction angles;
Δ: slight peaks at diffraction angles
X: clear peaks at diffraction angles;
—: could not be measured Further, a preparation that was stored in an unsealed state for a month at 40° C. (75% RH) with advanced crystallization of the test compound was examined for its absorbability using the same experiment as Example 7. As a result, the blood concentration in rats decreased to the same level as the administration of the bulk drug substance alone before amorphization, and a reduction in absorbability was observed (FIG. 5). Based on this result, it was once again confirmed that amorphization improves absorbability. On the other hand, the XRD of the test compound at the beginning of the experiment demonstrated, as in FIG. 6, that the compound was completely in the amorphous form, and the amorphous state was kept stable even after 1 month storage at 40° C. (75% RH) (FIG. 7). In contrast, the present test compound, which was stored in an unsealed state for 1 month at 40° C. (75% RH), was confirmed to have peaks at 2θ=7 to 10.0 that are characteristic to crystalline forms (FIG. 8).

Example 9

Manufacture of a 500 mg Tablet Comprising an Amorphous Body of the Test Compound 175 mg of the amorphous body of the test compound, 150 mg of a disintegrant (low-substituted hydroxypropyl cellulose, croscarmellose sodium and carmellose calcium etc.), 2.5 mg of a lubricant (calcium stearate and magnesium stearate etc.) were mixed by a V-type mixer for 15 min. at room temperature, and a roller-compactor was used to perform dry granulation to obtain granules.

The obtained granules were selected for an appropriate particle size using a sieve, and to these 170 mg of an excipient (crystalline cellulose, glucose, sucrose, lactose, D-mannitol and D-sorbitol etc.) and 2.5 mg of a lubricant (calcium stearate and magnesium stearate etc.) were added and mixed by a V-type mixer for 15 min. to obtain granules for tablet compression.

The granules for tablet compression were formed into tablets of 500 mg each using a rotary tablet press.

Formula for the preparation:

| | |
|---|---|
| Amorphous body of the test compound | 175 mg |
| Disintegrant | 150 mg |
| Excipient | 170 mg |
| Lubricant | 5 mg |

The present tablets were filled into a glass jar, sealed and evaluated for the stability of the amorphous body after 6 months of storage at 40° C. (75% RH). The XRD when the 500 mg tablet of the amorphous body of the test compound was produced showed, as in FIG. 9, that there were no identifiable peaks caused by crystallization at 2θ=7 to 10.0 at all, and only peaks caused by the disintegrant, excipient and lubricant, as shown in FIG. 10, were observed. Since peaks at 2θ=7 to 10.0 could not be identified at all in XRD after the 6-month storage, it was clear that the test compound in the present tablet was kept stable in the amorphous state (FIG. 11).

Additionally, the present invention is not limited by the amorphous body, solid dispersion, formulation and the method of production thereof explained using the above embodiments, which are meant to be disclosed as examples. The technical scope of the present invention is determined by the recitations of the claims, and it is possible for those skilled in the art to make various design changes within the technical scope of the invention as recited in the claims.

The invention claimed is:

1. An amorphous body composed of a heterocyclic compound represented by general formula (I):

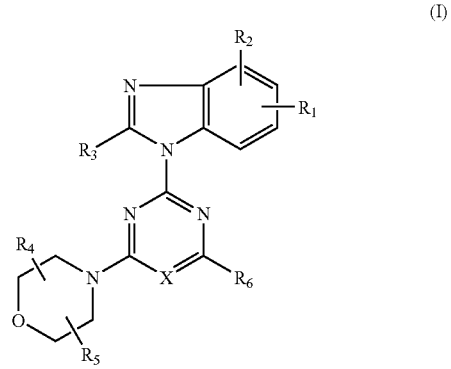

(I)

wherein, X represents a nitrogen atom or CH;
$R_1$ and $R_2$, both or either one, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a hydrogen atom, a difluoromethyl group, an amino group, a $C_1$-$C_6$ alkylamino group, a methyl, or a hydroxymethyl group;
$R_4$ and $R_5$ represent a hydrogen atom or a $C_1$-$C_6$ alkyl group; and
$R_6$ represents a morpholino, optionally substituted with 1 to 2 $C_1$-$C_6$ alkyl groups, a pyrrolidinyl, optionally substituted with a hydroxy $C_1$-$C_6$ alkyl group, a piperidino, optionally substituted with 1 to 2 oxygen atoms, a hydroxyl group, a formyl, or a $C_1$-$C_6$ alkyl group, a piperazinyl, optionally substituted with 1 to 2 oxygen atoms, the nitrogen at position 4 optionally substituted with a substituent selected from the group consisting of formyl, hydroxyl $C_1$-$C_6$ alkyl, $C_1$-$C_6$ alkoxycarbonyl, oxo $C_1$-$C_6$ alkyl, aromatic carbonyl, benzylcarbonyl and substituted carbamoyl, or a 1,4-diazepano, optionally substituted with 1 to 2 oxygen atoms, the nitrogen at position 4 optionally substituted with a substituent selected from the group consisting of formyl, hydroxy $C_1$-$C_6$ alkyl, $C_1$-$C_6$ alkoxycarbonyl, oxo $C_1$-$C_6$ alkyl, aromatic carbonyl, benzyl carbonyl and substituted carbamoyl; or a hydrate thereof, a solvate thereof, or a pharmaceutically acceptable salt thereof.

2. The amorphous body according to claim 1, produced by a spray drying method, a mixed grinding method, a fusion method or a solvent method.

3. A solid dispersion comprising the amorphous body according to claim 1 and a pharmaceutically acceptable solid polymer.

4. The solid dispersion according to claim 3, wherein said solid polymer is a cellulose derivative.

5. The solid dispersion according to claim 4, wherein said cellulose derivative is hydroxypropyl cellulose or hypromellose.

6. The solid dispersion according to claim 3, wherein the mass ratio of said heterocyclic compound, the hydrate thereof, the solvate thereof, or the pharmaceutically acceptable salt thereof and said solid polymer is 1:0.1 to 1:10.

7. The solid dispersion according to claim 6, wherein said mass ratio is 1:2 to 2.5.

8. The solid dispersion according to claim 3, further comprising an excipient, a disintegrant and a lubricant.

9. A formulation comprising the solid dispersion according to claim 3, provided in the form of a powder, a fine granule, a granule, a tablet or a capsule.

10. A method for producing an amorphous body composed of a heterocyclic compound represented by general formula (I):

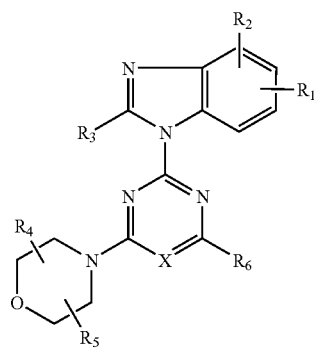

(I)

wherein, X represents a nitrogen atom or CH;

$R_1$ and $R_2$, both or either one, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;

$R_3$ represents a hydrogen atom, a difluoromethyl group, an amino group, a $C_1$-$C_6$ alkylamino group, a methyl, or a hydroxymethyl group;

$R_4$ and $R_5$ represent a hydrogen atom or a $C_1$-$C_6$ alkyl group; and $R_6$ represents a morpholino, optionally substituted with 1 to 2 $C_1$-$C_6$ alkyl groups, a pyrrolidinyl, optionally substituted with a hydroxy $C_1$-$C_6$ alkyl group, a piperidino, optionally substituted with 1 to 2 oxygen atoms, a hydroxyl group, a formyl, or a $C_1$-$C_6$ alkyl group, piperazinyl, optionally substituted with 1 to 2 oxygen atoms, the nitrogen at position 4 optionally substituted with a substituent selected from the group consisting of formyl, hydroxyl $C_1$-$C_6$ alkyl, $C_1$-$C_6$ alkoxycarbonyl, oxo $C_1$-$C_6$ alkyl, aromatic carbonyl, benzylcarbonyl and substituted carbamoyl, or a 1,4-diazepano, optionally substituted with 1 to 2 oxygen atoms, the nitrogen at position 4 optionally substituted with a substituent selected from the group consisting of formyl, hydroxy $C_1$-$C_6$ alkyl, $C_1$-$C_6$ alkoxycarbonyl, oxo $C_1$-$C_6$ alkyl, aromatic carbonyl, benzyl carbonyl and substituted carbamoyl; or a hydrate thereof, a solvate thereof, or a pharmaceutically acceptable salt thereof;

said method comprising dissolving said heterocyclic compound, the hydrate thereof, the solvate thereof or the pharmaceutically acceptable salt thereof in a solvent to prepare a feed solution;

spraying said feed solution; and drying the sprayed feed solution to obtain said amorphous body.

* * * * *